United States Patent
Renzel

(10) Patent No.: US 7,415,880 B2
(45) Date of Patent: Aug. 26, 2008

(54) METHOD FOR DETERMINING THE SOUND VELOCITY IN A BASIC MATERIAL, PARTICULARLY FOR MEASURING THE THICKNESS OF A WALL

(75) Inventor: Peter Renzel, Duren-Birgel (DE)

(73) Assignee: Agfa NTD GmbH (DE)

( * ) Notice: Subject to any disclaimer, the term of this patent is extended or adjusted under 35 U.S.C. 154(b) by 68 days.

(21) Appl. No.: 10/522,203

(22) PCT Filed: Jun. 27, 2003

(86) PCT No.: PCT/DE03/02150

§ 371 (c)(1),
(2), (4) Date: Mar. 3, 2006

(87) PCT Pub. No.: WO2004/017021

PCT Pub. Date: Feb. 26, 2004

(65) Prior Publication Data

US 2006/0191342 A1    Aug. 31, 2006

(30) Foreign Application Priority Data

Jul. 17, 2002 (DE) ................................. 102 32 475
Jun. 12, 2003 (DE) ................................. 103 27 102

(51) Int. Cl.
*G01N 29/00* (2006.01)

(52) U.S. Cl. .......................................... 73/597; 73/627

(58) Field of Classification Search ............ 73/596–600, 73/602, 627, 628, 629, 630
See application file for complete search history.

(56) References Cited

U.S. PATENT DOCUMENTS

| 4,088,028 A * | 5/1978 | Hildebrandt ................. 73/611 |
| 4,182,155 A * | 1/1980 | Fowler ....................... 73/1.81 |
| 5,894,092 A   | 4/1999 | Lindgren et al. |
| 6,035,717 A * | 3/2000 | Carodiskey .................. 73/597 |
| 6,070,466 A * | 6/2000 | Taran et al. ................. 73/622 |

FOREIGN PATENT DOCUMENTS

JP         5-288728      * 11/1993

* cited by examiner

*Primary Examiner*—Helen C. Kwok
(74) *Attorney, Agent, or Firm*—Cantor Colburn, LLP

(57) ABSTRACT

Disclosed is a method for determining the sound velocity (Cb) in a basic material, in which an ultrasonic probe having a transmitting probe, a receiver transducer, and a forward member is used. The forward member is provided with a coupling surface that couples the probe to the basic material, and has a sound velocity (Cv). The transmitting probe and the receiver transducer are aligned in an oblique manner from each other and from the coupling surface such that a main transmission direction of the transmitting probe and a main receiving direction of the receiver transducer intersect below the coupling surface. The centers of the transmitting probe and the receiver transducer are located at a distance K from each other and are located at a distance Dv from the coupling surface. According to the inventive method, the transmitting probe generates an ultrasonic pulse which runs through the forward member into the basic material, where the ultrasonic pulse creates a creeping wave, a portion of which arrives at the receiver transducer. The shortest sound traveling time (Ttot) is measured and the sound velocity (Cb) within the basic material is determined via the path between the transmitting probe and the receiver transducer, which supplies the shortest total traveling time (Ttot).

9 Claims, 2 Drawing Sheets

METHOD FOR DETERMINING THE SOUND VELOCITY IN A BASIC MATERIAL, PARTICULARLY FOR MEASURING THE THICKNESS OF A WALL

TECHNICAL FIELD OF INVENTION

The invention relates to a method for determining the sound velocity Cb in a base material, using an ultrasonic probe comprising a transmit crystal, a receive crystal and a precursor body, said precursor body a) having a coupling surface by which the probe is couplable to the base material, b) receiving the receive crystal and the transmit crystal and c) having a sound velocity Cv, the transmit crystal and the receive crystal being oriented to be inclined towards each other and each towards the coupling surface so that a main transmission direction of the transmit crystal and a main receiving direction of the receive crystal intersect below the coupling surface, transmit crystal and receive crystal being spaced apart at a center to center distance K, the transmit crystal being spaced at a center to center distance Ds from the coupling surface and the receive crystal at a distance De from the coupling surface, by which method an ultrasonic pulse is generated by the transmit crystal, passes through the precursor body into the base material where it produces a creeping wave a portion of which reaches the receive crystal via the precursor body, and to a corresponding device.

A prerequisite of the ability of determining the wall thickness of the base material is to determine the sound velocity Cb. Although it is known to determine the wall thickness of a base material by multiple reflection of a pulse at an entrance surface and at a back surface of the base material, this method makes sufficiently mirror-like and, as a result thereof, smooth surfaces, more specifically a sufficiently smooth back surface a provision for ensuring multiple forward and reflected pulse waves within the base material. This method cannot be used with rough back surfaces; in this case, one is dependent on a pulse wave that travels back and forth only once. The wall thickness may then be determined through the sound velocity Cb.

BRIEF DESCRIPTION OF RELATED ART

A method and a device for determining the thickness of a coated base material is known from U.S. Pat. No. 6,035,717. Using this method for determining the sound velocity Cb of the base material, the uncoated base material is first measured, a pulse is sent from a transmit crystal through the precursor body into the base material where a creeping wave is produced a portion of which being again decoupled and received by the receive crystal. Inasmuch, this patent coincides with the invention.

However, according to U.S. Pat. No. 6,035,717, the path of the pulse is assumed to be imposed. It appears that the inventor of said U.S. Patent Document was well aware of the fact that assuming a geometrically imposed path along the main beams will result in certain inaccuracies in determining the sound velocity Cb. He therefore gives practical instructions, proposing to keep the distance separating the two crystals from the coupling surface as small as possible. This actually makes determining the sound velocity in the base material more precise, so that, put another way, the inaccuracy is reduced. However, a probe the precursor body of which has a short sound travel distance suffers from the disadvantage that but little material of the precursor body is available for the wear occurring during each practical testing so that the probe needs to be replaced earlier than a probe having a greater precursor distance.

BRIEF SUMMARY OF THE INVENTION

The present invention provides a method of determining sound velocity Cb in the base material with greater accuracy so as to permit determining the thickness of a coating applied to said base material with greater accuracy as well and to allow using a probe the precursor distance of which is sufficiently thick.

The present invention measures the shortest sound travel time Ttot and by determining the sound velocity Cb in the base material via that path that delivers, as a function of the sound velocity, the shortest total travel time Ttot between transmit crystal and receive crystal.

This method takes into account that the path by which the pulse travels through the precursor body, along the surface of the base material (as the surface wave) and back to the precursor body is influenced not only by the previously known variables K, Dv and Cv (K=center to center distance between the contact surfaces of the crystals, Dv=center to center distance between the contact surface of a crystal and the coupling surface) but also by the sound velocity Cb. If, compared to the sound velocity Cv in the precursor body, said sound velocity Cb is relatively high, the portion of the travel distance Sb along the surface of the base material will also be relatively large. If, by contrast, the sound velocity Cb in the base material is relatively small, the travel distance Sb of the surface wave in the base material will be relatively short, with the travel distances Sv within the precursor body becoming longer. Similar conditions will prevail when light is reflected between different optical media such as water and air. In this case again, the geometrically shortest path for a light pulse is not the shortest in time.

The achievement of the invention is that it relies on the observation that in determining the shortest travel time Ttot of the ultrasound pulse and in optimizing all of the possible sound travel paths leading to the sound travel path that supplies the shortest total travel time as a function of Cb, one obtains precise information about the sound velocity Cb in the base material. Accordingly, the invention relies on the actual paths travelled by a sound pulse. It does not, as this is the case with U.S. Pat. No. 6,035,717, rely on any assumption about the path. Accordingly, the errors of this prior art measurement method and of the related device are thus avoided in accordance with the invention.

Further advantages and characteristics of the invention will become apparent upon reviewing the other claims and the following non restrictive description of embodiments of the invention, given by way of example only with reference to the drawing, as well as of the method in accordance with the invention.

In said drawing:

DETAILED DESCRIPTION OF THE INVENTION

Figure 1:
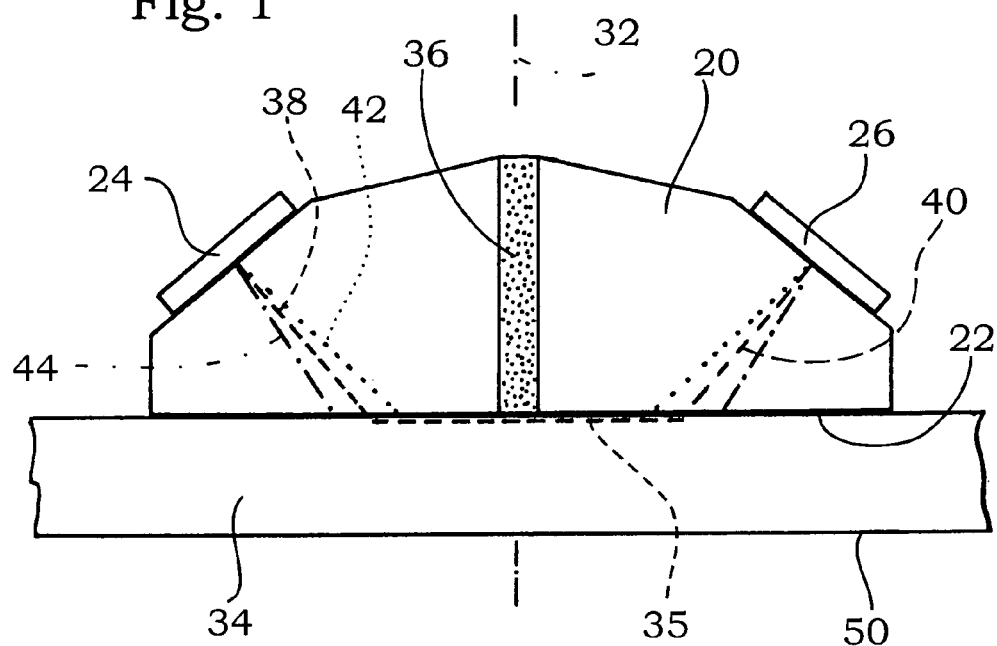
FIG. 1: is a schematic representation as viewed from the side of a probe having two crystals, said probe being coupled to a base material, and shows the various portions of the overall path.

The probe shown in FIG. 1 has a specially shaped, substantially prismatic precursor body 20. It has a level coupling surface 22, which is also referred to as the active surface, and, on the opposite side thereof, bevels on which a transmit crystal 24 and a receive crystal 26 are respectively retained, more specifically cemented. The two crystals 24, 26 are built according to the same principle. They are disposed at an incline toward each other and also relative to the coupling surface 22. This arrangement will be discussed in further detail herein after.

A perpendicular bisector, meaning a line that perpendicularly bisects said crystal contact surface with the precursor body 20, is inclined at a certain angle relative to the coupling surface 22, said angle being (90° −αv) and being the same for the two crystals 24, 26. Further, the respective perpendicular bisectors lie in the same plane, namely in the plane of FIG. 1.

This may also be put another way: the two crystals 24, 26 exhibit two-fold symmetry about a plane of symmetry 32. They are inclined to the coupling surface 22 in such a manner that a surface wave 35 is generated in a base material 34 to which the precursor body 20 is coupled by well-known suited means, this being discussed in further detail herein after.

A separating layer 36 provided substantially along the plane of symmetry 32 prevents direct cross talk between transmit crystal 24 and receive crystal 26.

The perpendicular bisectors indicated usually coincide with a main beam, i.e., with a main transmitting beam 38 and with a main receiving beam 40.

The sound velocity Cv in the precursor body 20 is known. The distance K between the surface centers of the two crystals 24, 26 is known as well. Finally, the distance of the surface center of the transmit crystal 24 from the coupling surface 22 and the distance of the center of the receive crystal 26 from the coupling surface 22 can be determined and are thus known. Due to symmetry, they both have the value Dv. With only these date, it is now possible to determine the sound velocity Cb in the base material 34. In a further step, the thickness, that is the wall thickness Db of the base material 34, can be determined.

If the sound velocity Cb in the base material 34 is approximately as high as the sound velocity of steel, the shortest path of a sound pulse from the transmit crystal 24 to the receive crystal 26 is as follows: the pulse travels along the main transmitting beam, then in the form of a surface wave 35 in the base material 34 and eventually along the main receiving beam 40 into the receive crystal 26. This path is shown in a dashed line in FIG. 1; it extends along the main transmitting beam 38 and along the main receiving beam 40.

If however the sound velocity Cb in the base material 34 is smaller than that of steel, the sound path will use as much of a distance as possible within the precursor body 20, with the length of the distance Sb realized by the surface wave 38 in the base material 34, shortening. This case is shown in FIG. 1 in which the sound travel path 42 is shown in a dotted line.

If conversely the sound velocity Cb in the base material is higher than that of steel, the sound distance Sv within the precursor body 20 becomes shorter, with the travel distance Sb in the form of the surface wave 35 becoming longer as a result thereof. This case is represented in FIG. 1 which shows the sound travel path 44 in a dash-dot line.

For simplicity's sake, FIG. 1 only shows in a dashed line the complete sound travel path extending along the main beams 38, 40. It can be seen that the travel distance Sb of the surface wave 35 is a function of the sound velocity Cb in the base material 34 and moreover depends on the constant variables K, Cv and Dv. In accordance with the invention, the sound velocity Cb in the base material 34 is obtained by optimizing the associated sound travel path. Accordingly, that sound travel path is taken as a basis that supplies the shortest total travel time Ttot as a function of the sound velocity Cb to be determined.

The greater the angle to the main beam, the more the amplitude of the sound pressure diminishes. If however one only measures the signal with the shortest total travel time Ttot, one is independent, within certain limits, of the amplitude of the receive signal. Ideally, the crystals 24, 26 should be spherical sources, but this is not the case. With the sound velocities obtained in practice, the fact that the crystals 24, 26 are not spherical has not such a great influence that this should be taken into consideration and specially evaluated. The orientation of the crystals 24, 26 ideally occurs for a mean value of the sound velocity Cb (e.g., for steel Cb about 6000 m/s).

Accordingly, the respective path by which the sound pulse with the shortest total travel time Ttot travels is function of the sound velocity Cb and further dependent on the known values K, Dv and Cv. If the structure does not exhibit two-fold symmetry, the various center-to-center distances of the transmit crystal 24 and of the receive crystal 26 from the coupling surface 22 must be taken into consideration.

According to FIG. 1, the ultrasound propagates from the transmit crystal 24 along a first path segment Sv until it reaches the base material 34, needing therefore the time Tv. There, a creeping wave 35 is generated. It has the length indicated in FIG. 2. It travels this length within time Tb. One portion of the creeping wave reaches the receive crystal 26 by a path which has, due to the symmetry, the length Sv and for which the time Tv is needed.

What is sought is the distance Sb between the starting point and the end point of the creeping wave or of the surface wave 35 respectively for longitudinal waves.

General formulas for sound propagation will be set forth herein after. Only the shortest total travel time Ttot will be considered. In order to determine the latter, it is necessary to take the total travel distance from the transmit crystal 24 to the receive crystal 26 into consideration. It will be assumed that K=center to center distance of the probe heads 24, 26; Dv=center to center distance of the crystals 24, 26 from the coupling surface 22 and Cv=sound velocity in the precursor body are known and time constant, for the short duration of the measurement at any rate.

An ultrasound pulse emitted by the transmit crystal 24 will not only effect a surface wave 35 in the base material 34, but other waves as well; the longitudinal surface wave 35 has the shortest travel distance and the shortest total travel time Ttot as well.

Figure 2:
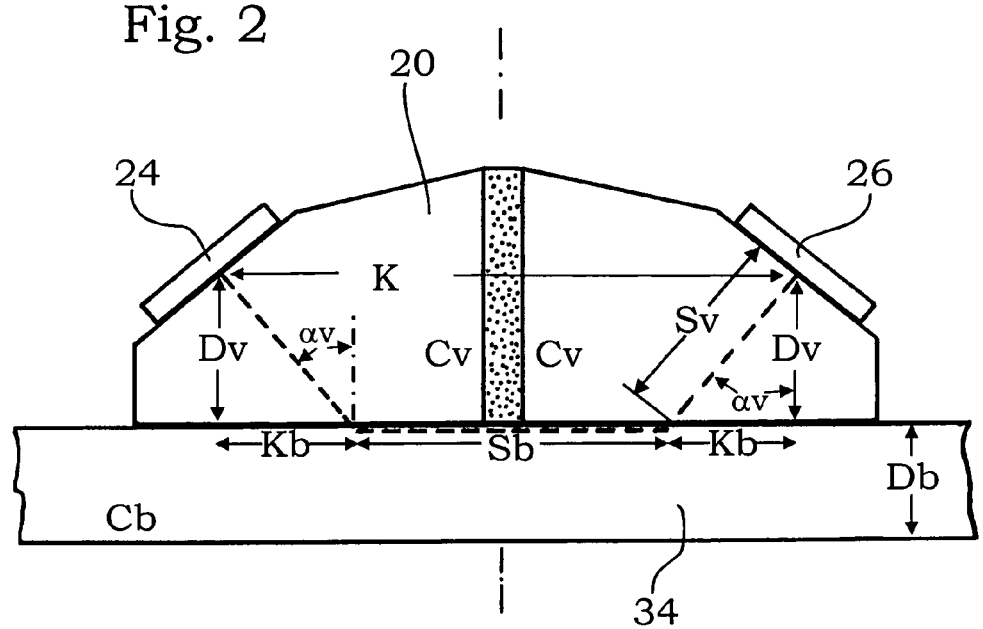
FIG. 2: is the representation according to FIG. 1 showing the travel distances, the sound velocities, and so on, FIG. 3: is a representation like FIG. 1 with the base material having now additionally a thin layer (a coating) such as a color, a metal coating or a plastic layer

According to FIG. 2, the following applies:

$$S_b = K - 2K_b; \quad (1)$$

$$\tan\alpha_v = \frac{K_b}{D_v}; \rightarrow K_b = D_v \tan\alpha_v; \quad (2)$$

$$S_b = K - 2D_v \tan\alpha_v; \quad (1/2) \quad (3)$$

Different sound travel paths differ by their entrance angle $\alpha_v$.

This angle is maintained with assumption of the shortest possible total travel time Ttot:

$$T_{tot} = 2T_v + T_b; \quad (4)$$

$$C_v = \frac{S_v}{T_v}; \rightarrow T_v = \frac{S_v}{C_v}; \quad (5)$$

$$C_b = \frac{S_b}{T_b}; \rightarrow T_b = \frac{S_b}{C_b}; \quad (6)$$

$$\cos \alpha_v = \frac{D_v}{S_v}; \rightarrow S_v = \frac{D_v}{\cos \alpha_v}; \quad (7)$$

$$T_v = \frac{D_v}{C_v \cos \alpha_v}; \quad (5/7) \quad (8)$$

$$T_{tot} = \frac{2D_v}{C_v \cos \alpha_v} + \frac{K - 2D_v \tan \alpha_v}{C_b}; \quad (4/8/3/6) \quad (9)$$

$$T_{tot} = \frac{K}{C_b} + 2D_v \left( \frac{1}{C_v \cos \alpha_v} - \frac{\tan \alpha_v}{C_b} \right); \quad (9) \quad (10)$$

What is sought is the minimum of the linear function Ttot (αv). This can for example be determined through the first derivation after the angle αv; the first derivation must be zero for a certain angle αv and the second derivation must be positive:

$$\frac{\partial T_{tot}(\alpha_v)}{\partial \alpha_v} = 0! \quad (11)$$

$$\frac{\partial T_{tot}(\alpha_v)}{\partial \alpha_v} = 2D_v \left( \frac{\sin \alpha_v}{C_v \cos^2 \alpha_v} - \frac{1}{C_b \cos^2 \alpha_v} \right) = 0; \quad (10) \quad (12)$$

$$\frac{\sin \alpha_v}{C_v} - \frac{1}{C_b} = 0; \rightarrow \sin \alpha_v = \frac{C_v}{C_b}; \rightarrow \alpha_v = \arcsin\left(\frac{C_v}{C_b}\right); \quad (12) \quad (13)$$

Taking now (3) into consideration, it will be recognized that the sound travel distance Sb is dependent on the two sound velocities Cv and Cb:

$$S_b = K - 2D_v \tan\left( \arcsin\left( \frac{C_v}{C_b} \right) \right); \quad (3/12) \quad (14)$$

As it can be assumed that K, Dv and Cv are constant, this means that Sb=f(Cb). The following equation (15) describes the dependency between the total travel time Ttot measured and the sound velocity Cb to be determined:

$$T_{tot} = \frac{K}{C_b} + 2D_v \left( \frac{1}{C_v \cos\left(\arcsin\left(\frac{C_v}{C_b}\right)\right)} - \frac{\tan\left(\arcsin\left(\frac{C_v}{C_b}\right)\right)}{C_b} \right); \quad (9/12) \quad (15)$$

As a result, a clear correlation between the total travel time Ttot and the sound velocity Cb to be determined is achieved. All the other variables in the equation (15) are known and constant.

Accordingly, it is clearly possible to determine the sound velocity Cb in the base material from the total travel time Ttot. This finding now permits to determine the wall thickness Db of the base material.

Figure 3:
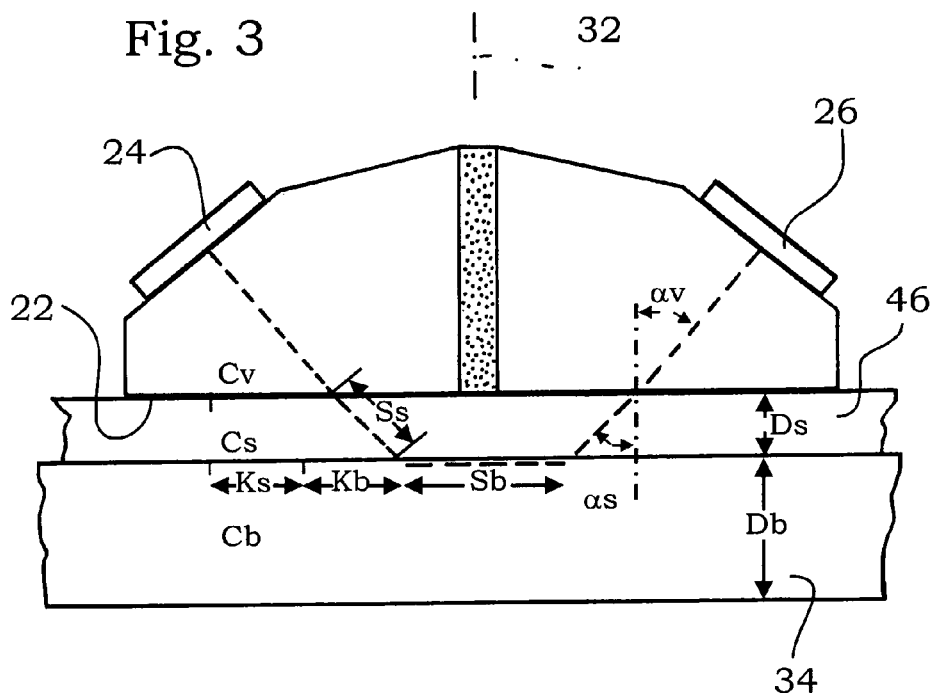

FIG. 3 shows the arrangement of the previous FIGS. with the base material 34 now having an additional layer 46, a so-called coating. This layer has a thickness Ds. It is to be determined from the sound velocity Cs of the layer. As the latter is not known either, the sound velocity is determined first like before.

FIG. 3 again only shows the sound travel distance with the shortest total travel time Ttot. Other propagations also occur, a surface wave is for example also generated at the surface of the coating 46 that is turned toward the coupling surface 22, but this wave is to occur in time after the surface wave 35 in the base material 34. This means that the sound velocity Cb in the base material 34 has to be sufficiently higher than the sound velocity Cs in the layer 46. In practice, this is mostly the case. Typically, the base material is a metal, the sound velocities range from 4500 to 7000 m/s. The layer 46 typically is a plastic material, a color or the like; the sound velocities typically range from 2000 to 3000 ms. In the event the sound velocity Cs in the layer 46 is relatively high, for example if the layer is a metal coating on a base material made from plastic material, the layer consists of a metal having a higher sound velocity than the base material, e.g., if the coating is made from Ag and the base material from Au, it must be proceeded according to the above mentioned considerations, simply by utilizing the layer 46 as the base material.

Herein after, the sound travel path shown in FIG. 3 is considered the shortest travel path. In the layer 46, the entrance angle αv is changed to as. The travel distances in the volume of the layer 46 are apparent from FIG. 3; they amount to Ss. The associated sound travel time is Ts.

For the shortest total travel time, the following then applies:

$$T_{tot} = 2(T_v + T_s) + T_b; \quad (16)$$

$$C_v = \frac{S_v}{T_v}; \rightarrow T_v = \frac{S_v}{C_v}; \quad (17)$$

$$\cos \alpha_v = \frac{D_v}{S_v}; \rightarrow S_v = \frac{D_v}{\cos \alpha_v}; \quad (18)$$

$$T_v = \frac{D_v}{C_v \cos \alpha_v}; \quad (17/18) \quad (19)$$

In the layer 46, the conditions are the same; for the layer 46, the following applies:

$$T_s = \frac{D_s}{C_s \cos \alpha_s}; \quad (19) \quad (20)$$

$$T_b = \frac{S_b}{C_b}; \quad (21)$$

$$S_b = K - 2(K_b + K_s); \quad (22)$$

$$\tan \alpha_v = \frac{K_s}{D_v}; \rightarrow K_s = D_v \tan \alpha_v; \quad (23)$$

$$\tan \alpha_s = \frac{K_b}{D_s}; \rightarrow K_b = D_s \tan \alpha_s; \quad (24)$$

$$S_b = K - 2(D_s \tan \alpha_s + D_v \tan \alpha_v); \quad (22/23/24) \quad (25)$$

$$T_b = \frac{K - 2(D_s \tan \alpha_s + D_v \tan \alpha_v)}{C_b}; \quad (21/25) \quad (26)$$

Now all the elements for Ttot are known:

$$T_{tot} = 2\left(\frac{D_v}{C_v \cos \alpha_v} + \frac{D_s}{C_s \cos \alpha_s}\right) + \frac{K - 2(D_s \tan \alpha_s + D_v \tan \alpha_v)}{C_b}; \quad (27)$$

$$T_{tot} = \frac{2D_v}{C_v \cos \alpha_v} + \frac{2D_s}{C_s \cos \alpha_s} + \frac{K}{C_b} - \frac{2D_s \tan \alpha_s}{C_b} - \frac{2D_v \tan \alpha_v}{C_b}; \quad (27) \quad (28)$$

$$T_{tot} = \frac{K}{C_b} + 2\left(D_v\left(\frac{1}{C_v \cos \alpha_v} - \frac{\tan \alpha_v}{C_b}\right) + D_s\left(\frac{1}{C_s \cos \alpha_s} - \frac{\tan \alpha_s}{C_b}\right)\right); \quad (29)$$
(28)

Now, the total travel time Ttot is not only a function of the entrance angle $\alpha v$ (like in (15)), but also a function of the entrance angle $\alpha s$ and can be represented as follows:

$$T_{tot}(\alpha_v, \alpha_s) = \frac{K}{C_b} + 2(f_1(\alpha_v) + f_2(\alpha_s)); \quad (29) \quad (30)$$

If the function Ttot($\alpha v$, $\alpha s$) has a minimum this can again be established from the first derivation after the two angles. The first derivations must be 0:

$$\frac{\partial f_1(\alpha_v)}{\partial \alpha_v} = 0! \quad (31)$$

$$\frac{\partial f_2(\alpha_s)}{\partial \alpha_s} = 0! \quad (32)$$

$$\frac{\partial f_1(\alpha_v)}{\partial \alpha_v} = D_v\left(\frac{\sin \alpha_v}{C_v \cos^2 \alpha_v} - \frac{1}{C_b \cos^2 \alpha_v}\right) = 0 \quad (31/29) \quad (33)$$

$$\frac{\sin \alpha_v}{C_v} - \frac{1}{C_b} = 0; \rightarrow \frac{\sin \alpha_v}{C_v} = \frac{1}{C_b}; \rightarrow \sin \alpha_v = \frac{C_v}{C_b}; \quad (34)$$

$$\rightarrow \alpha_v = \arcsin\left(\frac{C_v}{C_b}\right); \quad (33)$$

$$\frac{\partial f_2(\alpha_s)}{\partial \alpha_s} = D_s\left(\frac{\sin \alpha_s}{C_s \cos^2 \alpha_s} - \frac{1}{C_b \cos^2 \alpha_s}\right) = 0 \quad (32/29) \quad (35)$$

$$\frac{\sin \alpha_s}{C_s} - \frac{1}{C_b} = 0; \rightarrow \frac{\sin \alpha_s}{C_s} = \frac{1}{C_b}; \rightarrow \sin \alpha_s = \frac{C_s}{C_b}; \quad (36)$$

$$\rightarrow \alpha_s = \arcsin\left(\frac{C_s}{C_b}\right); \quad (35)$$

The results (34) and (36) are now inserted into the equation (29) which yields:

$$T_{tot} = \frac{K}{C_b} + 2\left(D_v\left(\frac{1}{C_v \cos \arcsin\left(\frac{C_v}{C_b}\right)} - \frac{\tan \arcsin\left(\frac{C_v}{C_b}\right)}{C_b}\right) + D_s\left(\frac{1}{C_s \cos \arcsin\left(\frac{C_s}{C_b}\right)} - \frac{\tan \arcsin\left(\frac{C_s}{C_b}\right)}{C_b}\right)\right); \quad (29/34/36) \quad (37)$$

Figure 4:
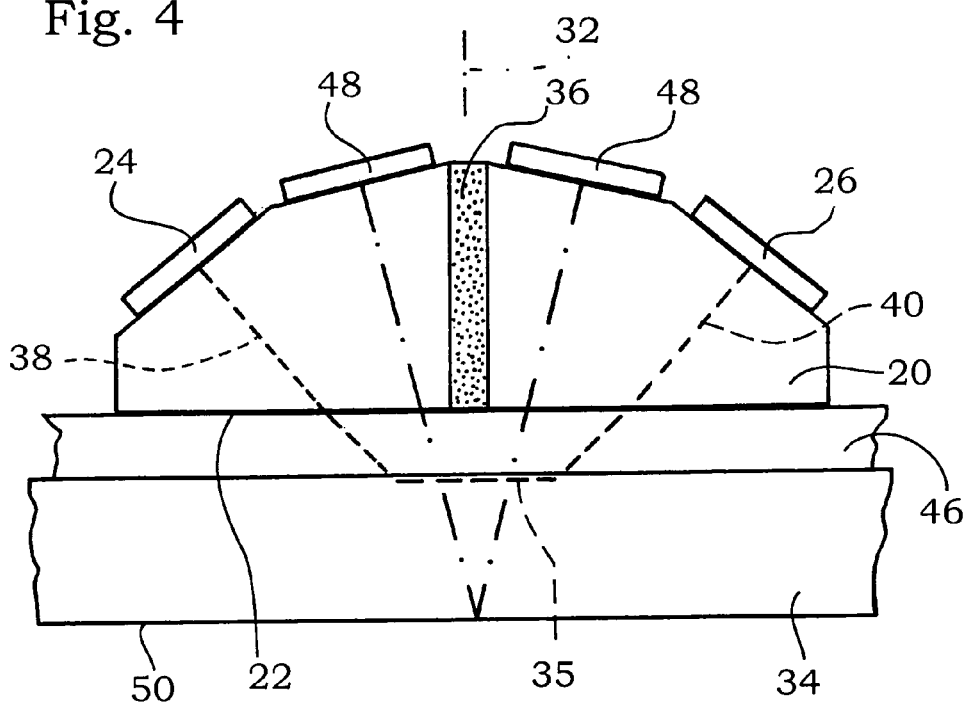
FIG. 4: is a representation like FIG. 1 but now with two additional crystals for measuring the wall thickness.

The shortest total travel time Ttot can be measured using a suited measuring instrument, for example the apparatus DMS 2 of the applicant. From this total travel time, the thickness Ds of the layer 46 or the thickness Db of the base material 34 can now be determined, provided the sound velocities Cs and Cb are known. Cb for example can be determined at an uncoated site of the body being tested, using (27). Through an additional pair of crystals for thickness measurement with the crystals 48, which are built according to the same principle, the sound energy is emitted at a steep angle, as can be seen from FIG. 4. A back wall echo is generated the travel time of which is reduced by the travel time of Ds. The thickness Db of the base material is calculated therefrom with the sound velocity Cb being known.

A second echo, which occurs next in time, is obtained from a back wall 50 of the base material 34. The thickness Db of the base material 34 can be determined from the time difference between the two echoes and from the previously measured sound velocity Cb in said base material. The thickness Db can also be obtained as the difference between this echo of the back wall 50 and the entrance echo, taking into consideration the sound velocities and deducing the thickness Ds of the layer 46.

The following connections will become apparent or clear from the equation (37):
1)

$$\frac{C_v}{C_b} \text{ and } \frac{C_s}{C_b}$$

must be smaller than 1;9
2) $C_s$ can be smaller than $C_v$.

The invention claimed is:

1. A method for determining sound velocity Cb in a base material of a specimen to be tested, using an ultrasonic probe, the probe comprising: a transmitting transducer; a receiving transducer; and a precursor body; said precursor body: a) having a coupling surface by which the probe is couplable to the base material, b) carrying the receiving transducer and the transmitting transducer, and c) having a sound velocity Cv; said transmitting transducer and said receiving transducerbeing oriented to be inclined towards each other and each towards the coupling surface so that a main transmission direction of the transmitting transducer and a main receiving direction of the receiving transducer intersect below the coupling surface; said transmitting transducer and receiving transducerbeing spaced apart at a center to center distance K; said transmitting transducer and said receiving transducer being spaced at a center to center distance Dv from the coupling surface;
said method comprising:
generating an ultrasonic pulse by the transmitting transducer which is passed through the precursor body into the base material;
the ultrasonic pulse producing a creeping wave in the base material, the creeping wave being a surface wave, at least a portion of the creeping wave reaching the receiving transducer via the precursor body; and
measuring a shortest sound travel time Ttot of the ultrasonic pulse and the sound velocity Cb in the base material by a path between the transmitting transducer and the receiving transducer that supplies the shortest total travel time Ttot.

2. The method according to claim 1, wherein the path that supplies the shortest total travel time Ttot is determined by summing a travel distance from the transmitting transducer to the base material, a travel distance within the base material and a travel distance from the base material to the receiving transducer and by optimizing said travel distances with regard to the shortest total travel time Ttot.

3. The method according to claim 1, wherein the shortest total travel time Ttot is obtained through $$T_{tot} = \frac{K}{Cb} + 2Dv\left(\frac{1}{Cv\cos\left(\arcsin\left(\frac{Cv}{Cb}\right)\right)} - \frac{\tan\left(\arcsin\left(\frac{Cv}{Cb}\right)\right)}{Cb}\right).$$

4. The method according to claim 1, wherein main beams of the transmitting transducer and the receiving transducer lie in the same plane, the main beams being inclined at the same angle relative to a coupling surface.

5. The method according to claim 1, further including determining sound velocity in a coating material applied as a layer on base material, the method comprising:
   placing the probe onto the layer having a thickness Ds;
   generating an ultrasound pulse by the transmitting transducer that traverses both the precursor body and the layer at an incline toward the coupling surface;
   producing a creeping wave in the base material a portion of which creeping wave again traverses the layer and the precursor body at an incline toward the coupling surface prior to reaching the receiving transducer;
   registering and measuring a receive signal with the shortest total travel time Ttot; and
   determining the coating thickness Ds of the layer from that path that supplies the shortest total travel time Ttot.

6. The method according to claim 5, wherein the shortest travel time Ttot is obtained from $$Ttot = \frac{K}{Cb} + 2\left(Dv\left(\frac{1}{Cv\cos\arcsin\left(\frac{Cv}{Cb}\right)} - \frac{\tan\arcsin\left(\frac{Cv}{Cb}\right)}{Cb}\right) + Ds\left(\frac{1}{Cs\cos\arcsin\left(\frac{Cs}{Cb}\right)} - \frac{\tan\arcsin\left(\frac{Cs}{Cb}\right)}{Cb}\right)\right),$$

wherein Ds=the thickness of the layer.

7. The method according to claim 1, wherein the path that supplies the shortest total travel time Ttot is determined by summing up a travel distance from the transmitting transducer to the base material, a travel distance within the base material and a travel distance from the base material to the receiving transducer and by differentiation after the angle.

8. A device for determining sound velocity Cb in a base material of a specimen to be tested, comprising:
   an ultrasonic probe comprising: a transmitting transducer; a receiving transducer; and a precursor body;
   said precursor body: a) having a coupling surface by which the probe is couplable to the base material, b) carrying the receiving transducer and the transmitting transducer, and c) having a sound velocity Cv;
   said transmitting transducer and said receiving transducer being oriented to be inclined towards each other and each towards the coupling surface so that a main transmission direction of the transmitting transducer and a main receiving direction of the receiving transducer intersect below the coupling surface;
   said transmitting transducer and said receiving transducer being spaced apart at a center to center distance K; and
   said transmitting transducer and said receiving transducer being spaced at a center to center distance Dv from the coupling surface,
   wherein the transmitting transducer is configured to generate an ultrasonic pulse which passes through the precursor body into the base material, wherein the ultrasonic pulse produces a creeping wave in the base material, the creeping wave being a surface wave, a portion of the creeping wave being configured to reach the receiving transducer via the precursor body, and wherein the shortest sound travel time Ttot of the ultrasonic pulse is measurable and the sound velocity Cb in the base material is determinable by the very path between the transmitting transducer and the receiving transducer that supplies the shortest total travel time Ttot.

9. The device of claim 8, wherein main beams of the transmitting transducer and said receiving transducer lie in the same plane, the main beams inclined at the same angle relative to the coupling surface.

* * * * *